United States Patent
Zhu et al.

(10) Patent No.: US 8,859,795 B2
(45) Date of Patent: Oct. 14, 2014

(54) PROCESS FOR PRODUCING ESTER OF CARBOXYLIC ACID FROM CELLULOSIC BIOMASS

(75) Inventors: Zuolin Zhu, San Diego, CA (US); Meg M. Sun, San Diego, CA (US); Chungao Su, Huaibei (CN); Hongping Ye, Huaibei (CN)

(73) Assignee: Sun Pharmaceuticals, Inc., San Diego, CA (US)

( * ) Notice: Subject to any disclaimer, the term of this patent is extended or adjusted under 35 U.S.C. 154(b) by 296 days.

(21) Appl. No.: 13/497,286

(22) PCT Filed: Sep. 22, 2009

(86) PCT No.: PCT/CN2009/074087
§ 371 (c)(1),
(2), (4) Date: May 30, 2012

(87) PCT Pub. No.: WO2011/035463
PCT Pub. Date: Mar. 31, 2011

(65) Prior Publication Data
US 2012/0245367 A1   Sep. 27, 2012

(51) Int. Cl.
*C07C 69/00* (2006.01)
*C07C 67/00* (2006.01)

(52) U.S. Cl.
CPC .................................. *C07C 67/00* (2013.01)
USPC ............................................................ 554/142

(58) Field of Classification Search
CPC ............................... C07C 67/00; C07C 69/24
See application file for complete search history.

*Primary Examiner* — Deborah D Carr
(74) *Attorney, Agent, or Firm* — Lee & Hayes, PLLC

(57) ABSTRACT

The invention discloses a technology for producing ester of carboxylic acid using cellulosic biomass as starting material. This technology comprises the following key steps: converting all of the organic polymers, including such high molecular-weight polymers as carbohydrate components and lignin, in cellulosic biomass into water soluble, small molecular organics completely in relatively short time under relatively mild conditions; separating the resultant water soluble compounds containing aromatic rings by adjusting the acidity/basicity of the reaction solution or by using adsorption resin; and converting the water soluble compounds containing aromatic rings into ester of carboxylic acid by hydrogenation and esterification in a corresponding alcohol solution.

17 Claims, No Drawings

PROCESS FOR PRODUCING ESTER OF CARBOXYLIC ACID FROM CELLULOSIC BIOMASS

CROSS REFERENCE TO RELATED APPLICATIONS

This application is a 35 U.S.C. 371 national stage application of International Application No. PCT/CN2009/074087, filed Sep. 22, 2009, the entire contents of which is incorporated herein by reference.

TECHNICAL FIELD

The invention relates to preparation of esters of organic acid, particularly to a method and process technique for producing ester of carboxylic acid using cellulosic biomass as starting material.

BACKGROUND

Ester of carboxylic acid is a kind of very important chemical raw material, pharmaceutical intermediates, fragrances, etc., and may also be used as liquid fuels, such as biodiesel and biogasoline. Biodiesel as people talk about today broadly means ester of carboxylic acid produced from aliphatic acids and small molecular alcohols. The well-known biodiesel is aliphatic esters of methanol, as methanol is the cheapest alcohol. Methyl carboxylates prepared from animal fat and vegetable oil are regarded as the most ideal substitute for diesel, because they contain neither sulfur aromatic compounds nor nitrogen aromatic compounds, and thus, when burning, will not produce sulfur oxides, nitrogen oxides and the like which are the most predominant environmental pollutants.

Nowadays, commercially available products of ester of carboxylic acid are almost all prepared from petroleum, coal, foodstuff as well as edible animal fat and vegetable oil as starting materials through a series of reactions. Particularly, the starting materials of the biodiesel used currently in large quantities are exclusively animal fat and vegetable oil which, as the traditional and customary human food, are already very short in view of population. As indicated by a UN statistical source in June, 2009, there are presently over 1 billion people in a state of famine. Therefore, it is deemed as a crime against humanity to take human food for other purposes.

Cellulosic biomass is the largest, annually renewable organic carbon resource on the earth. However, it is mostly discarded as waste. If a process is developed to prepare chemical raw materials, pharmaceutical intermediates, fragrances, etc., such as ester of carboxylic acid, by using cellulosic biomass as a starting material, then not only the starvation problem of a considerable proportion of the population will be solved due to substantially reduced consumption of foodstuff, but also the production cost of ester of carboxylic acid including biodiesel will be lowered somewhat along with the change of cellulosic biomass from waste to treasure.

Therefore, a process for preparing chemical raw materials, pharmaceutical intermediates, fragrances, etc. by refining cellulosic biomass, such as preparing ester of carboxylic acid from cellulosic biomass, is extremely important to sustainable development of human beings.

SUMMARY OF THE INVENTION

The object of the invention is to provide a process for preparing ester of carboxylic acid including biodiesel from cellulosic biomass instead of petroleum, coal, foodstuff as well as edible animal fat and vegetable oil as a starting material.

According to the invention, a process for producing ester of carboxylic acid is provided, which comprises the following steps:

(a) converting the organic polymers in cellulosic biomass into water soluble organics;

(b) separating to obtain water soluble organics containing aromatic rings; and (c) hydrogenating and esterifying the water soluble organics containing aromatic rings to obtain ester of carboxylic acid.

In another preferred embodiment, a catalyst is used in step (a), wherein the catalyst is selected from single-ring or fused-ring substances as shown by Formulae 1A, 1B, 2A or 2B, or substances having their resonance structures, metallic compounds or combinations thereof;

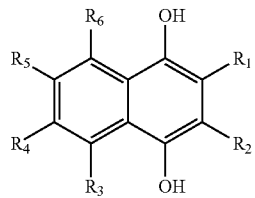

1A

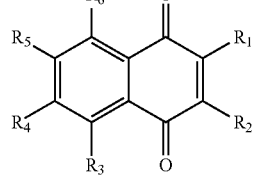

1B

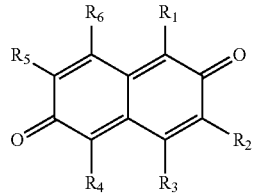

2A

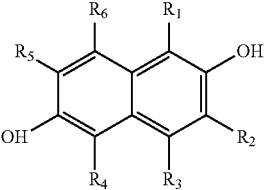

2B wherein $R_1$, $R_2$, $R_3$, $R_4$, $R_5$, $R_6$ are linear alkyl groups having 1-18 carbons, branched alkyl groups having 1-18 carbons, alkenyl groups having 1-18 carbons or aromatic ring groups having 1-18 carbons; wherein the hydrogen atoms on the linear alkyl groups, branched alkyl groups or alkenyl groups may be all present as they are or may be substituted by halogen, oxygen, sulfur and/or nitrogen.

In another preferred embodiment, $R_1$, $R_2$, $R_3$, $R_4$, $R_5$, $R_6$ are hydroxyl groups (OH), carboxyl groups (COOH), amino groups ($NH_2$), mercapto groups (SH), nitro groups, sulfonic groups ($SO_3H$) and/or halogen atoms.

In another preferred embodiment, the hydrogen(s) on the hydroxyl groups (OH), carboxyl groups (COOH), amino groups (NH$_2$), mercapto groups (SH), nitro groups or sulfonic groups (SO$_3$H) may be substituted by saturated or unsaturated carbons.

In another preferred embodiment, any two of R$_1$, R$_2$, R$_3$, R$_4$, R$_5$, R$_6$ groups on ortho-positions may represent another fused-ring. For example, R$_1$ and R$_2$ may constitute another aromatic ring, such as a six-member ring (including two carbons that couple R$_1$ and R$_2$ to the original ring respectively, such as the structures shown by Formulae 1A' and 1B', wherein the fused ring as such characterized may be further coupled with other fused rings or functional groups). It can be analogized that R$_3$ and R$_4$ may constitute another aromatic ring, R$_4$ and R$_5$ may constitute still another aromatic ring, R$_5$ and R$_6$ may constitute yet another aromatic ring, and so on. In Formulae 2A and 2B, R$_3$ and R$_4$ are regarded as being on ortho-positions and may constitute another aromatic ring. The same is true for R$_1$ and R$_6$.

In another preferred embodiment, the substances shown by Formulae 1A, 1B, 2A or 2B are biological extracts.

In another preferred embodiment, the metallic compounds are metallic salts of organic acids and inorganic acids, water soluble metallic hydroxides, metallic hydrides, metallic oxides, metallic peroxides.

In another preferred embodiment, the metal is selected from alkali metal, alkaline earth metal or transition metal.

In another preferred embodiment, the organic acids are C1-6 organic acids; the hydroxides are selected from lithium hydroxide, sodium hydroxide, potassium hydroxide, beryllium hydroxide, magnesium hydroxide, calcium hydroxide, strontium hydroxide or barium hydroxide; the oxides are selected from lithium oxide, sodium oxide, potassium oxide, beryllium oxide, magnesium oxide, calcium oxide, strontium oxide or barium oxide; and the salts of inorganic acids are selected from carbonates, halates, sulfates, nitrates, hypohalites, perhalates, phosphates or silicates.

In another preferred embodiment, the reaction in step (a) is carried out under alkaline condition.

In another preferred embodiment, the alkaline condition is provided by the presence of excessive base in the reaction system, wherein the base is selected from lithium hydroxide, sodium hydroxide, potassium hydroxide, rubidium hydroxide, cesium hydroxide, francium hydroxide, beryllium hydroxide, magnesium hydroxide, calcium hydroxide, strontium hydroxide, barium hydroxide, radium hydroxide, lithium oxide, sodium oxide, potassium oxide, rubidium oxide, cesium oxide, francium oxide, beryllium oxide, magnesium oxide, calcium oxide, strontium oxide, barium oxide, radium oxide, lithium carbonate, sodium carbonate, potassium carbonate, rubidium carbonate, cesium carbonate, francium carbonate, beryllium carbonate, magnesium carbonate, calcium carbonate, strontium carbonate, barium carbonate or radium carbonate.

In another preferred embodiment, pH value is adjusted to 0-7 in step (b) to obtain the water soluble organics containing aromatic rings by separation.

In another preferred embodiment, adsorption resin is used to separate the water soluble organics containing aromatic rings by adsorption.

In another preferred embodiment, the alcohol solution of the water soluble organics containing aromatic rings is catalytically hydrogenated in step (c).

In another preferred embodiment, the catalyst used is selected from catalysts commonly used for hydrogenation, and the solid phase catalyst is treated with a salt of alkali metal or alkaline earth metal; wherein the salt of alkali metal or alkaline earth metal is selected from sulfates, nitrates, carbonates or halates.

As such, the invention provides a process for producing ester of carboxylic acid by refining cellulosic biomass.

SPECIFIC MODES FOR CARRYING OUT THE EMBODIMENTS

Cellulosic biomass (or lignocellulosic biomass) used in the invention is defined as cellulose-containing biomass comprising cellulose, hemicellulose, lignin, protein and the like as its primary organic polymers, such as various hard wood, soft wood, barks, leaves, roots, canes, wild grass, reed, bamboo, water plants, crop waste including but not limited to corn stalk, sorghum stalk, wheat straw, bean stalk, rape stalk, peanut seedling, yam seedling, herbaceous fruit seedling, cotton stalk, etc.

According to the invention, all of the organic polymers in the cellulosic biomass are first degraded into water soluble small molecules. The catalyst for degradation is an organometallic compound, wherein the organic ligand is characterized by a derivative of a single-ring arene or a fused-ring arene containing two or more rings, comprising two oxygen functional groups on para-positions of the same ring, such as the substances shown by Formulae 1A and 1B as well as substances having their resonance structures:

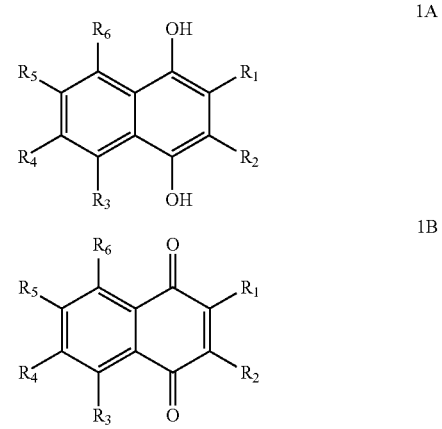

In Formulae 1A and 1B, R$_1$, R$_2$, R$_3$, R$_4$, R$_5$, R$_6$ are linear alkyl groups having 1-18 carbons, branched alkyl groups having 1-18 carbons, alkenyl groups having 1-18 carbons or aromatic ring groups. The hydrogen atoms on the linear alkyl groups, branched alkyl groups or alkenyl groups may be all present as they are or may be substituted by halogen, oxygen, sulfur, nitrogen, etc.

Alternatively, R$_1$, R$_2$, R$_3$, R$_4$, R$_5$, R$_6$ may be hydroxyl groups (OH), carboxyl groups (COOH), amino groups (NH$_2$), mercapto groups (SH), nitro groups, sulfonic groups (SO$_3$H) and halogen atoms. If they are not halogen atoms, the hydrogen atoms on these non-halogen groups may be substituted by saturated or unsaturated carbons.

Any two of R$_1$, R$_2$, R$_3$, R$_4$, R$_5$, R$_6$ groups on orthopositions may represent another fused ring. For example, R$_1$ and R$_2$ may constitute another aromatic ring, such as a six-member ring (including two carbons that couple R$_1$ and R$_2$ to the original ring respectively, such as the structures shown by Formulae 1A' and 1B', wherein the fused ring as such characterized may be further coupled with other fused rings or functional groups). It can be analogized that R$_3$ and R$_4$ may constitute another aromatic ring, R$_4$ and R$_5$ may constitute still another aromatic ring, $R_5$ and $R_6$ may constitute yet another aromatic ring, and so on.

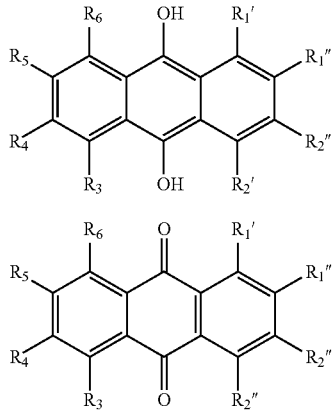

The ligand as described above further has a double-oxygen conjugated structure, such as the molecules shown by Formulae 2A and 2B.

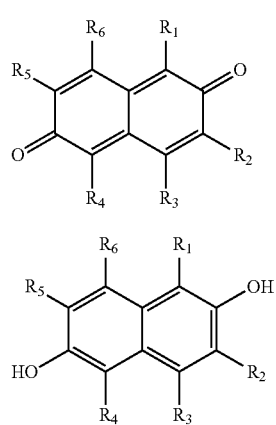

$R_1$, $R_2$, $R_3$, $R_4$, $R_5$, $R_6$ in Formulae 2A and 2B are defined the same way as in Formulae 1A and 1B. In Formulae 2A and 2B, $R_3$ and $R_4$ may be regarded as being on ortho-positions. Likewise, $R_1$ and $R_6$ may be regarded as being on ortho-positions.

The catalyst may be used after preparation and purification. Alternatively, it may be used immediately after an organic compound as described above and a metallic compound are directly mixed.

The metallic compounds may be metallic salts of organic acids and inorganic acids, water soluble metallic hydroxides, metallic hydrides, metallic oxides, metallic peroxides, etc. While any salt of an organic acid may be useful, an organic acid having 6 carbons or less is preferred in terms of cost. The metal is a monovalent, divalent or trivalent metallic ion, including alkali metal, alkaline earth metal and transition metal. The hydroxides of alkali metal include but are not limited to lithium hydroxide, sodium hydroxide, potassium hydroxide, etc. The hydroxides of alkaline earth metal are, for example, beryllium hydroxide, magnesium hydroxide, calcium hydroxide, strontium hydroxide, barium hydroxide, etc. The oxides of alkali metal include but are not limited to lithium oxide, sodium oxide, potassium oxide, etc. The oxides of alkaline earth metal include but are not limited to beryllium oxide, magnesium oxide, calcium oxide, strontium oxide, barium oxide, etc. The transition metal is any metallic ion that may be present in monovalent, bivalent and trivalent states. The salts of inorganic acids include all known salts of inorganic acids, including but not limited to carbonates, halates, sulfates, nitrates, hypohalites, perhalates, phosphates, silicates, etc.

Organic acid may be generated during the reaction in which cellulosic biomass is degraded into water soluble small molecules. In order to prevent gasification and carbonization, excessive base may be present in the reaction system to neutralize the resultant organic acid and keep the reaction system alkaline constantly. The base may be any alkaline substance, including but not limited to hydroxides of alkali metal, such as lithium hydroxide, sodium hydroxide, potassium hydroxide, rubidium hydroxide, cesium hydroxide, francium hydroxide, etc.; and hydroxides of alkaline earth metal, such as beryllium hydroxide, magnesium hydroxide, calcium hydroxide, strontium hydroxide, barium hydroxide, radium hydroxide, etc. The base may also be an oxide of an alkali metal, such as lithium oxide, sodium oxide, potassium oxide, rubidium oxide, cesium oxide, francium oxide, etc. The base further includes an oxide of an alkaline earth metal, such as beryllium oxide, magnesium oxide, calcium oxide, strontium oxide, barium oxide, radium oxide, etc. Carbonates of alkali metal, such as lithium carbonate, sodium carbonate, potassium carbonate, rubidium carbonate, cesium carbonate, francium carbonate, etc., and carbonates of alkaline earth metal, such as beryllium carbonate, magnesium carbonate, calcium carbonate, strontium carbonate, barium carbonate or radium carbonate, etc., may also be used. Monovalent, divalent and trivalent hydroxides, oxides and carbonates of transition metal may be useful as well.

The amount of the catalyst used is generally 0.1%-10% (by weight of the cellulosic biomass). Although the reaction may also be catalyzed if the amount of the catalyst used is out of the above range, the amount of the catalyst used that is lower than the above range is not preferred due to slow reaction rate, and the amount of the catalyst used that is higher than the above range is neither preferred due to excessively high cost.

The reaction process generally includes the following steps.

1. The cellulosic biomass is comminuted;
2. The cellulosic biomass is converted into water soluble substance;
3. The product containing aromatic rings is isolated;
4. The substance containing aromatic rings is hydrogenated and esterified to ester of carboxylic acid using alcohol as solvent.

The cellulosic biomass is generally comminuted to a particle size of less than 2 mm. Larger particle size is possible, but the reaction rate is relatively slow. Smaller particle size is also possible, but more energy is needed to comminute the cellulosic biomass into very small particles.

The reaction to convert the cellulosic biomass into water soluble substance is generally carried out in water, although other proton solvents may be used as well.

The reaction to convert the cellulosic biomass into water soluble substance is generally carried out at a temperature of 100-300° C. A temperature of lower than 100° C. is possible but not preferred for the reaction will be rather slow. A temperature of higher than 300° C. is also possible but neither preferred due to occurrence of gasification and carbonization.

The reaction to convert the cellulosic biomass into water soluble substance does not need applied pressure. The reaction generally needs 1 minute to 24 hours.

After all the organic polymers in the cellulosic biomass are completely degraded into water soluble substance, the reaction to convert the cellulosic biomass into water soluble substance is generally cooled to below 100° C. first, and then pH value of the reaction solution is adjusted. Most of the product containing aromatic rings is precipitated as solid under acidic condition. Separation of the solid product may be fulfilled by any conventional solid-liquid separation method.

In the product of the reaction converting the cellulosic biomass into water soluble substance, some compounds containing aromatic rings are hard to become solid. These compounds are small molecular phenols which may be vacuum distilled off or adsorbed by adsorption resin.

Macroporous adsorption resin capable of adsorbing phenols selectively is generally used as the resin for extraction of phenolic compounds by adsorption.

All of the compounds containing aromatic rings in the product are hydrogenated and esterified in the reactions for preparation of ester of carboxylic acid, generally using methanol as solvent due to the low price of methanol. Other alcohols may also be used but are not preferred due to their high prices.

Any conventional catalyst for hydrogenation may be used as the catalyst in the hydrogenation and esterification. If a conventional solid-phase catalyst is used, the catalyst is generally treated with some common salts of alkali metal or alkaline earth metal, and the treated catalyst may be used to effect the synchronous hydrogenation and esterification of the compounds containing aromatic rings as obtained above to give a product of ester of carboxylic acid. The salts of alkali metal or alkaline earth metal include but are not limited to sulfates, nitrates, carbonates, halates, and the like.

In the hydrogenation and esterification of the compounds containing aromatic rings obtained from the water soluble substance which is derived from cellulosic biomass, the hydrogen pressure is generally 1-80 kilograms. A pressure of lower than 1 kilogram is not preferred for the reaction will be rather slow. A pressure of higher than 80 kilograms is neither preferred for the cost will be rather high.

The reaction for converting cellulosic biomass into water soluble substance may be carried out in a Batch reactor system or a Continuous flow reactor system or a Flow through reactor system.

The process for producing ester of carboxylic acid from cellulosic biomass as disclosed in the invention is adapted to any biomass containing cellulose, including but not limited to fresh or dry cellulosic biomass, such as various hard wood, soft wood, barks, leaves, roots, canes, wild grass, reed, bamboo, water plants; cellulose-containing offal from agriculture, forestry, vegetable, fruit and sugar processing industries, cellulose-containing dung of various animals, cellulose-containing offal from traditional Chinese medicine processing industry; crop castoffs including but not limited to corn stalk, sorghum stalk, wheat straw, bean stalk, rape stalk, cotton stalk, sesame stalk, peanut seedling, yam seedling, herbaceous fruit seedling, cotton stalk, etc.

The invention will be further illustrated with reference to the following specific examples. It is to be understood that these examples are merely intended to demonstrate the invention without limiting the scope of the invention. The experimental methods in the following examples for which no specific conditions indicated will be carried out generally under conventional conditions or under those conditions suggested by the manufacturers. Unless otherwise specified, all percentages, ratios, proportions or parts are based on weight.

The unit of weight/volume percentage in the invention is well known to those skilled in the art, for example, referring to the weight of a solute in 100 mL solution.

Unless otherwise defined, all special and scientific terms used herein have the same meaning as that familiar to those skilled in the art. In addition, any method and material similar or equivalent to those cited herein may be used in the method of the invention. The preferred implementing methods and materials described herein are intended to be exemplary only.

EXAMPLES

Example 1

Preparation of Ester of Carboxylic Acid I

Conversion of cellulosic biomass into water soluble substance 300 g wheat stalk (dry weight), 3000 mL pure water, 0.8 g anthraflavic acid and 121 g sodium hydroxide were added into a stainless steel autoclave. The autoclave was sealed, heated to 240° C., and kept under the temperature for 3 hours.

After cooling to room temperature, filtration was carried out. The resultant solid was washed with pure water and vacuum dried. The final weight of the solid was 4.5 g, and the ash was determined to be 92%.

2. Extraction of Compounds Containing Aromatic Rings

The pH value of the liquid from which the solid product was filtered off was adjusted to around 3 using 30% sulfuric acid. The liquid was centrifuged to separate out 43 g undissolved brownish black product (P1) which was washed with pure water and then vacuum dried.

The liquid from which the undissolved product was separated out was passed through a column (inner diameter=3 cm) of 800 g non-ionic macroporous adsorption resin DA201C. The adsorption column was then washed with 1000 mL pure water, and the resin was further washed with 500 mL methanol. A grey black liquid was obtained, and the methanol was removed under vacuum to obtain 19 g black product (P2). The total yield of the products (P1+P2) was 20.6%.

3. Preparation of Ester of Carboxylic Acid

A tubular reactor (inner diameter=6 mm) with 10 mL admission space was loaded with 10 g 5% palladium/carbon (Pd/C) and plugged with glass wool at both ends. The reactor was then washed for 2 hours using pure water deoxygenated with nitrogen at 50° C. at a flow rate of 0.1 mL/min. Subsequently, a saturated solution of potassium sulfate in methanol which was deoxygenated with nitrogen was allowed to flow through the reactor at 50° C. at a flow rate of 0.1 mL/min for 6 hours. Finally, the reactor was treated for 2 hours by flowing 120° C./2 MPa hydrogen/pure methanol at a flow rate of 0.5 mL/min therethrough.

The brownish black product P1 obtained from wheat stalk was formulated into a 10% solution in methanol (weight/volume ratio) and passed through the tubular reactor along with 160° C./1 MPa hydrogen at flow rate of 0.05 mL/min. After cooling, a colorless and transparent liquid was obtained.

A GC/MS instrument (Agilent GC7890/MSD5973N) was used to analyze the reaction product in which no aromatic compound was detected. The product was comprised of methyl octadecanoate (m/e=298), methyl hexadecanoate (m/e=270), dimethyl 2-methyl-glutarate (m/e=174), dimethyl glutarate (m/e=160), methyl 2-hydroxyl-pentanoate (m/e=114, MW-18), dimethyl succinate (m/e=146), methyl hexanoate (m/e=130), dimethyl adipate (m/e=174), dimethyl 2-ethyl-adipate (m/e=202), etc.

After 1000 mL 10% solution of the brownish black product P1 in methanol was reacted and then the methanol was distilled off, 110 g product of ester of carboxylic acid I was obtained. A similar result was obtained from the hydrogenation and esterification of the product P2.

Examples A-D

Conversion of Cellulosic Biomass into Water Soluble Substance

A: Under nitrogen protection and agitation, a solution of two equivalents of sodium hydroxide in ethanol was added dropwise into a solution of 20 g 2,6-dihydroxyanthraquinone in ethanol in a suitable vessel. After the addition was completed, agitation was continued for 30 minutes, and then ethanol was removed by distillation to obtain an off-white solid V.

300 g corn stalk (dry weight), 3000 mL pure water, 0.8 g off-white solid catalyst V and 120 g sodium hydroxide were added into a stainless steel autoclave. The autoclave was sealed, heated to 240° C., and kept under the temperature for 3 hours.

After cooling to room temperature, filtration was carried out. The resultant solid was washed with pure water and vacuum dried. The final weight of the solid was 12 g, and the ash was determined to be 98.2%.

B: 300 g corn stalk (dry weight), 3000 mL pure water, 0.8 g 2,6-dihydroxyanthraquinone and 121 g sodium hydroxide were added into a stainless steel autoclave. The autoclave was sealed, heated to 240° C., and kept under the temperature for 3 hours.

After cooling to room temperature, filtration was carried out. The resultant solid was washed with pure water and vacuum dried. The final weight of the solid was 11 g, and the ash was determined to be 98.6%.

C: Reactions were carried out under the same conditions as in B except that different organics were used. Each group of data were averages from three tests. Corn stalk was used as the starting material, and corresponding conversions were obtained.

| Organic Compound | Solid remnant after reaction (g) | Solid ash content (%) | Proportion of unconverted stalk (%) |
|---|---|---|---|
| Fumigatin | 14.5 | 86 | 4.8 |
| Anthraflavic acid | 2.9 | 96.5 | 1 |
| 1-amino-4-bromo-2-methyl anthraquinone | 10.9 | 88 | 3.6 |
| Anthrarobin | 17.3 | 82 | 5.8 |
| Chrysophanol | 11.6 | 88 | 3.8 |
| Anthraquinone-2-sulfonic acid sodium salt | 28.9 | 69 | 9.6 |
| Hypericin | 14.8 | 85 | 4.9 |
| Anthrarufin | 25.5 | 67 | 8.5 |
| Benzoquinone | 17.9 | 82 | 5.8 |
| Benzo[a]anthracene-7,12-dione | 22.1 | 66 | 7.4 |
| Hydrojuglone | 11.6 | 89 | 3.8 |

The results showed that all conversions were higher than 90%.

D: Reactions were carried out under the same conditions as in B except that the organic compound used was anthraflavic acid and cellulosic biomass of different sources was used. Each group of data were averages from three tests. Respective conversions were obtained.

| Cellulosic biomass | Solid remnant after reaction (g) | Solid ash content (%) | Proportion of unconverted stalk (%) |
|---|---|---|---|
| Wheat stalk | 4.5 | 92 | 1.5 |
| Corn stalk | 2.9 | 96.5 | 1 |
| Bean stalk | 6.9 | 88 | 2.3 |
| Cottonseed husk | 4.8 | 92 | 1.6 |
| Bagasse | 11.6 | 88 | 3.8 |
| Reed | 8.9 | 89 | 2.9 |
| Pennisetum | 4.8 | 92 | 1.6 |
| Moso bamboo | 15.3 | 87 | 5.1 |
| Pine wood | 7.1 | 88 | 2.4 |
| Poplar wood | 7.1 | 91 | 2.4 |
| Rape stalk | 16.3 | 79 | 5.4 |

The results showed that more than 94% organic polymers were converted into water soluble, small molecular compounds with cellulosic biomass from different sources according to the invention.

Examples 2-11

Extraction of Compounds Containing Aromatic Rings

The pH value of the liquid from which the solid product was filtered off in Example D was adjusted to around 3 using 30% sulfuric acid. The liquid was centrifuged to separate out undissolved brownish black product P1 which was washed with pure water and then vacuum dried.

The liquid from which the undissolved product was separated out was passed through a column (inner diameter=3 cm) of 800 g non-ionic macroporous adsorption resin DA201C. The adsorption column was then washed with 1000 mL pure water, and the resin was further washed with 500 mL methanol. A grey black liquid was obtained, and the methanol was removed under vacuum to obtain black product P2.

The table below showed the yields of the resultant compounds containing aromatic rings, which were averages from three tests.

| Cellulosic biomass | Brownish black product P1 (g) | Black product P2 (g) | (P1 + P2) product yield (%) |
|---|---|---|---|
| Wheat stalk | 43 | 19 | 20.6 |
| Corn stalk | 33 | 21 | 18 |
| Bean stalk | 43 | 12 | 18 |
| Cottonseed husk | 51 | 33 | 28 |
| Bagasse | 32 | 28 | 20 |
| Reed | 32 | 40 | 24 |
| Pennisetum | 33 | 20 | 18 |
| Moso bamboo | 54 | 39 | 31 |
| Pine wood | 46 | 38 | 28 |
| Poplar wood | 27 | 33 | 20 |
| Rape stalk | 36 | 30 | 22 |

Example 13

Preparation of Ester of Carboxylic Acid

A tubular reactor (inner diameter=6 mm) with 10 mL admission space was loaded with 10 g 5% palladium/carbon (Pd/C) and plugged with glass wool at both ends. The reactor was then washed for 2 hours using pure water deoxygenated with nitrogen at 50° C. at a flow rate of 0.1 mL/min. Subsequently, a saturated solution of potassium sulfate in methanol which was deoxygenated with nitrogen was allowed to flow through the reactor at 50° C. at a flow rate of 0.1 mL/min for 6 hours. Finally, the reactor was treated for 2 hours by flowing 120° C./2 MPa hydrogen/pure methanol at a flow rate of 0.5 mL/min therethrough.

The brownish black product P1 obtained from wheat stalk in Example 2 was formulated into a 10% solution in methanol (weight/volume ratio) and passed through the tubular reactor along with 160° C./1 MPa hydrogen at flow rate of 0.05 mL/min. After cooling, a colorless and transparent liquid was obtained.

A GC/MS instrument (AgilentGC7890/MSD5973N) was used to analyze the reaction product in which no aromatic compound was detected. The product was comprised of methyl octadecanoate (m/e=298), methyl hexadecanoate (m/e=270), dimethyl 2-methyl-glutarate (m/e=174), dimethyl glutarate (m/e=160), methyl 2-hydroxyl-pentanoate (m/e=114, MW-18), dimethyl succinate (m/e=146), methyl hexanoate (m/e=130), dimethyl adipate (m/e=174), dimethyl 2-ethyl-adipate (m/e=202), etc.

After 1000 mL 10% solution of the brownish black product P1 in methanol was reacted and then the methanol was distilled off, 110 g product of ester of carboxylic acid was obtained.

The compounds containing aromatic rings obtained from cellulosic biomass of different sources and the compositions of the products obtained from hydrogenation and esterification of these compounds are similar with each other. The only difference among these esters is the proportions of these esters. For example, the content of methyl octadecanoate in the product of the ester of carboxylic acid prepared from wheat stalk was about 3%, while that of methyl octadecanoate in the product of the ester of carboxylic acid prepared from poplar wood was about 1.4%.

The invention claimed is:

1. A process for producing ester of carboxylic acid, comprising the following steps:
   (a) converting the organic polymers in cellulose biomass into water soluble organics;
   (b) separating to obtain water soluble organics containing aromatic rings; and
   (c) hydrogenating and esterifying the water soluble organics containing aromatic rings to obtain ester of carboxylic acid.

2. The process of claim 1, wherein a catalyst is used in step (a), the catalyst is selected from single-ring hydroquinone or fused-ring substances as shown by Formulae 1A, 1B, 2A or 2B, or substances having their resonance structures, metallic compounds or combinations thereof:

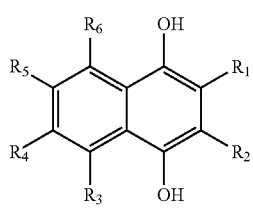

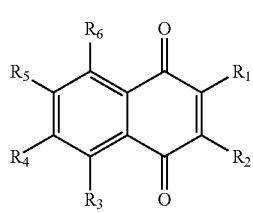

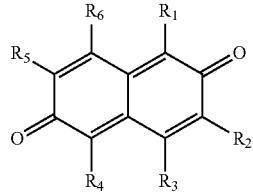

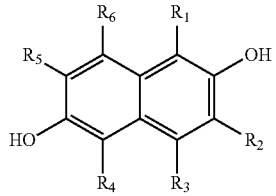

wherein $R_1$, $R_2$, $R_3$, $R_4$, $R_5$, $R_6$ are linear alkyl groups having 1-18 carbons, branched alkyl groups having 1-18 carbons, alkenyl groups having 1-18 carbons or aromatic ring groups; the hydrogen atoms on the linear alkyl groups, branched alkyl groups or alkenyl groups may be all present as they are or may be substituted by halogen, oxygen, sulfur and/or nitrogen.

3. The process of claim 2, wherein $R_1$, $R_2$, $R_3$, $R_4$, $R_5$, $R_6$ are hydroxyl groups (OH), carboxyl groups (COOH), amino groups ($NH_2$), mercapto groups (SH), nitro groups, sulfonic groups ($SO_3H$) and/or halogen atoms.

4. The process of claim 3, wherein the hydrogen(s) on the hydroxyl groups (OH), carboxyl groups (COOH), amino groups ($NH_2$), mercapto groups (SH), nitro groups or sulfonic groups ($SO_3H$) may be substituted by saturated or unsaturated carbons.

5. The process of claim 2, wherein the metallic compounds are metallic salts of organic acids and inorganic acids, water soluble metallic hydroxides, metallic hydrides, metallic oxides, metallic peroxides.

6. The process of claim 5, wherein the metal is selected from alkali metal, alkaline earth metal or transition metal.

7. The process of claim 5, wherein the organic acids are C1-6 organic acids; the hydroxides are selected from lithium hydroxide, sodium hydroxide, potassium hydroxide, beryllium hydroxide, magnesium hydroxide, calcium hydroxide, strontium hydroxide or barium hydroxide; the oxides are selected from lithium oxide, sodium oxide, potassium oxide, beryllium oxide, magnesium oxide, calcium oxide, strontium oxide or barium oxide; and the salts of inorganic acids are selected from carbonates, halates, sulfates, nitrates, hypohalites, perhalates, phosphates or silicates.

8. The process of claim 1, wherein the reaction in step (a) is carried out under alkaline condition.

9. The process of claim 8, wherein the alkaline condition is provided by the presence of excessive base in the reaction system, wherein the base is selected from lithium hydroxide, sodium hydroxide, potassium hydroxide, rubidium hydroxide, cesium hydroxide, francium hydroxide, beryllium hydroxide, magnesium hydroxide, calcium hydroxide, strontium hydroxide, barium hydroxide, radium hydroxide, lithium oxide, sodium oxide, potassium oxide, rubidium oxide, cesium oxide, francium oxide, beryllium oxide, magnesium oxide, calcium oxide, strontium oxide, barium oxide, radium oxide, lithium carbonate, sodium carbonate, potassium carbonate, rubidium carbonate, cesium carbonate, francium carbonate, beryllium carbonate, magnesium carbonate, calcium carbonate, strontium carbonate, barium carbonate or radium carbonate.

10. The process of claim 1, wherein pH value is adjusted to 0-7 in step (b) to obtain the water soluble organics containing aromatic rings by separation.

11. The process of claim 10, wherein separating the water soluble organics containing aromatic rings by adsorption resin.

12. The process of claim 1, wherein the hydrogenating and esterifying the water soluble organics comprises preparing an alcohol solution of the water soluble organics containing aromatic rings that is catalytically hydrogenated in step (c).

13. The process of claim 12, wherein the catalyst used is selected from catalysts commonly used for hydrogenation, and the solid phase catalyst is treated with a salt of alkali metal or alkaline earth metal; wherein the salt of alkali metal or alkaline earth metal is selected from sulfates, nitrates, carbonates or halates.

14. A composition of organic esters prepared by a process comprising:
(a) converting organic polymers in cellulose biomass into water soluble organics;
(b) separating the water soluble organics containing aromatic rings; and
(c) hydrogenating and esterifying the water soluble organics containing aromatic rings to obtain the composition of organic esters, wherein the composition comprises methyl octadecanoate, methyl hexadecanoate, dimethyl 2-methyl-glutarate, dimethyl glutarate, methyl 2-hydroxyl-pentanoate, dimethyl succinate, methyl hexanoate, dimethyl adipate, and dimethyl 2-ethyl-adipate.

15. The composition of claim 14, wherein the reaction in step (a) is carried out under alkaline conditions and at a temperature of 100° C. to 300° C.

16. The composition of claim 14, wherein the cellulose biomass is selected from the group consisting of various hard wood, soft wood, barks, leaves, roots, canes, wild grass, reed, bamboo, water plants; corn stalk, sorghum stalk, wheat straw, bean stalk, rape stalk, cotton stalk, sesame stalk, peanut seedling, yam seedling, herbaceous fruit seedling, and cotton stalk.

17. The process of claim 1, wherein the cellulose biomass is selected from the group consisting of various hard wood, soft wood, barks, leaves, roots, canes, wild grass, reed, bamboo, water plants; corn stalk, sorghum stalk, wheat straw, bean stalk, rape stalk, cotton stalk, sesame stalk, peanut seedling, yam seedling, herbaceous fruit seedling, and cotton stalk.

* * * * *

UNITED STATES PATENT AND TRADEMARK OFFICE
CERTIFICATE OF CORRECTION

PATENT NO. : 8,859,795 B2  
APPLICATION NO. : 13/497286  
DATED : October 14, 2014  
INVENTOR(S) : Zuolin Zhu et al.

Page 1 of 1

It is certified that error appears in the above-identified patent and that said Letters Patent is hereby corrected as shown below:

On the Title Page, item (73) Assignee, please change

"Sun Pharmaceuticals, Inc., San Diego, CA (US)" to

--China Fuel (HUAIBEI) Bioenergy Technology Development Co. Ltd, Huaibei (CN)  
Sun Pharmaceuticals, Inc., San Diego, CA (US)--.

Signed and Sealed this  
Twentieth Day of October, 2015

Michelle K. Lee  
*Director of the United States Patent and Trademark Office*